United States Patent
Paulus et al.

(10) Patent No.: US 10,352,882 B2
(45) Date of Patent: Jul. 16, 2019

(54) METHOD AND SYSTEM FOR ANALYZING AN OBJECT BY DIFFRACTOMETRY USING A SCATTERING SPECTRUM AND A TRANSMISSION SPECTRUM

(71) Applicant: Commissariat A L'Energie Atomique et Aux Energies Alternatives, Paris (FR)

(72) Inventors: Caroline Paulus, Grenoble (FR); Joachim Tabary, Grenoble (FR)

(73) Assignee: COMMISSARIAT A L'ENERGIE ATOMIQUE ET AUX ENERGIES ALTERNATIVES, Paris (FR)

( * ) Notice: Subject to any disclaimer, the term of this patent is extended or adjusted under 35 U.S.C. 154(b) by 271 days.

(21) Appl. No.: 15/322,611

(22) PCT Filed: Jun. 25, 2015

(86) PCT No.: PCT/FR2015/051714
§ 371 (c)(1),
(2) Date: Dec. 28, 2016

(87) PCT Pub. No.: WO2016/001536
PCT Pub. Date: Jan. 7, 2016

(65) Prior Publication Data
US 2017/0153189 A1    Jun. 1, 2017

(30) Foreign Application Priority Data
Jun. 30, 2014 (FR) ..................... 14 56186

(51) Int. Cl.
*G01N 23/20* (2018.01)
*G01N 23/201* (2018.01)
(Continued)

(52) U.S. Cl.
CPC ..... *G01N 23/20083* (2013.01); *G01N 23/087* (2013.01); *G01N 23/201* (2013.01);
(Continued)

(58) Field of Classification Search
CPC ......... G01N 23/2076; G01N 23/20025; G01N 23/20091; G01N 2223/316
(Continued)

(56) References Cited

U.S. PATENT DOCUMENTS

| | | |
|---|---|---|
| 4,956,856 A | 9/1990 | Harding |
| 5,428,657 A | 6/1995 | Papanicolopoulos |

(Continued)

FOREIGN PATENT DOCUMENTS

| | | |
|---|---|---|
| EP | 0311177 A2 | 4/1989 |
| EP | 2075571 A1 | 7/2009 |
| WO | WO2006/0075296 A1 | 7/2006 |

OTHER PUBLICATIONS

Pani, S. et al., "Characterization of breast tissue using energy-dispersive X-ray diffraction computed tomography".
(Continued)

*Primary Examiner* — Courtney D Thomas
(74) *Attorney, Agent, or Firm* — Brinks Gilson & Lione (57) ABSTRACT

A method for analyzing an object includes irradiating the object with incident photon radiation and acquiring an energy spectrum scattered by the material using a spectrometric detector in scatter mode. An energy spectrum transmitted by the material is acquired using a spectrometric detector in transmission mode. A signature (f) is reconstructed representing the object, both from the scatter spectrum measured and from the transmission spectrum measured, and the reconstructed signature thereof is compared with signatures of standard materials.

14 Claims, 9 Drawing Sheets

(51) Int. Cl.
*G01N 23/087* (2018.01)
*G01N 23/207* (2018.01)
(52) U.S. Cl.
CPC ..... *G01N 23/2076* (2013.01); *G01N 2223/04* (2013.01); *G01N 2223/045* (2013.01); *G01N 2223/304* (2013.01); *G01N 2223/3037* (2013.01); *G01N 2223/316* (2013.01); *G01N 2223/50* (2013.01)
(58) Field of Classification Search
USPC .................................................. 378/70–89
See application file for complete search history.

(56) References Cited

U.S. PATENT DOCUMENTS

| | | | |
|---|---|---|---|
| 7,092,485 B2* | 8/2006 | Kravis | G01N 23/20 378/57 |
| 2009/0168958 A1 | 7/2009 | Cozzini et al. | |
| 2012/0133516 A1 | 5/2012 | Harding | |
| 2016/0223706 A1* | 8/2016 | Franco | G01V 5/0025 |

OTHER PUBLICATIONS

International Search Report issued in PCT application PCT/FR2015/051714 dated Sep. 29, 2015, 6 pages.

\* cited by examiner

METHOD AND SYSTEM FOR ANALYZING AN OBJECT BY DIFFRACTOMETRY USING A SCATTERING SPECTRUM AND A TRANSMISSION SPECTRUM

RELATED APPLICATIONS

This application is a Section 371 nationalization of PCT application No. PCT/FR2015/051714, filed Jun. 25, 2015, the entire contents of which are incorporated by reference herein.

TECHNICAL FIELD

The present invention concerns a method of analyzing an object by diffractometry, and an associated detection system.

BACKGROUND

Diffractometry relates to the irradiation of a material or object using a source of electromagnetic radiation, of X or gamma type, followed by the analysis of radiation from elastic scattering at a small angle. The expression "radiation from elastic scattering at a small angle" designates the radiation coherently scattered by the material or object at an angle less than 15°, or less even than 10°, relative to the direction of the radiation that is incident on the material or object. As a matter of fact, beyond 10°, elastic scattering, or Rayleigh scattering, becomes progressively negligible.

It is known to use diffractometry to detect certain crystalline substances such as most explosives or numerous other dangerous or illegal structures.

The invention thus finds an application in the field of security, more particularly in the field of the detection of explosive materials in an item of baggage.

It is also useful in the medical field, for example for locating a tumor in a breast. More particularly, a publication by UCL (Pani, S. et al. "Characterization of breast tissue using energy-dispersive X-ray diffraction computed tomography". *Applied Radiation and Isotopes* 68, No. 10 (2010): 1980-1987) has been able to show the possibility of differentiating (adipose tissues, fibrous tissues, benign tumors, fibroadenomas, carcinomas, etc.) objects of biological tissues from breast biopsies thanks to the diffraction measurement of these tissues.

The analysis of the radiation scattered at a small angle (it is to be noted that that the term "diffracted" is generally used for a crystalline material, whereas the term "scattered" is generally used for an amorphous material, but these two terms here are used interchangeably, and likewise for the terms scattering and diffraction) by a material is a method of physico-chemical analysis which provides information on the structure of the material thereby enabling better characterization of materials.

It is known that the analysis of the spectrum of the radiation scattered at a small angle, or scattering spectrum, makes it possible to establish a signature for the material examined.

For crystalline materials for example, when the wavelength of the irradiating X-rays is of the same order of magnitude as the interplanar spacing (a few angstroms), the scattered rays generate constructive or destructive interferences according to their energy and their scattering angle. The conditions for which the interferences are constructive are determined by Bragg's law. For a crystalline material, this law links the interplanar spacing, the scattered radiation energy and the scattering angle, according to the following equation:

with:

$$E_{hkl} = n \frac{hc}{2d_{hkl}\sin(\theta/2)}$$

$d_{hkl}$: interplanar spacing between the crystallographic planes of the irradiated crystal;
{hkl}: Miller indices
θ: scattering angle, that is to say the angle formed between the scattered ray analyzed and the beam that is incident on the irradiated crystal
h: Planck's constant
c: the speed of light
n: the order of the interference.

It is possible to identify the Bragg peaks by the momentum transfer defined by the following equation:

$$x = \frac{\sin(\theta/2)}{\lambda} = \frac{n}{2d_{hkl}}$$

The interest in expressing the scattering profiles (measured intensity) according to x is due to the fact that an intensity peak may be measured for different pairs (λ,θ) but for a single value of x (n fixed).

In the case of non-crystalline materials, the spectrum for scattering at a small angle is also representative of the material examined.

Figure 1:
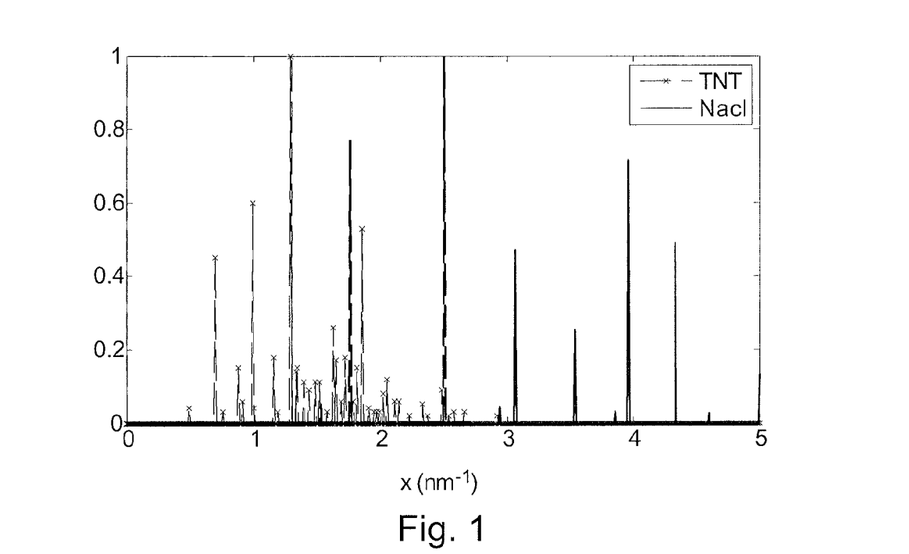
FIG. 1 is a graph representing the Bragg peaks of TNT (trinitrotoluene) and of salt (NaCl), which peaks illustrate the normalized intensity (y-axis), that is to say the relative number of photons detected during an acquisition operation, according to the momentum transfer x (x-axis) in $nm^{-1}$ of the detected photons.

By way of examples, appended FIG. 1 shows the Bragg peaks of two crystals, TNT (trinitrotoluene) and salt (NaCl).

Figure 2:
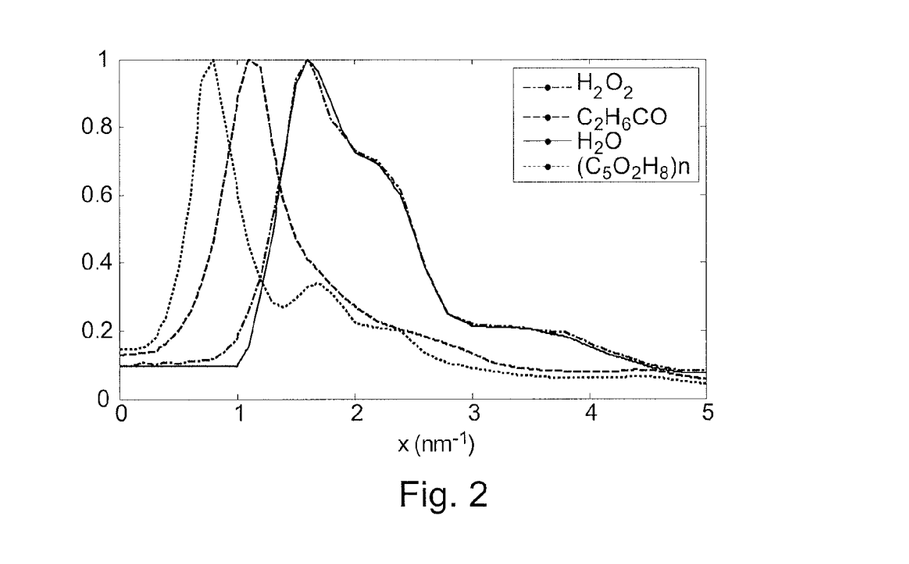
FIG. 2 is a graph representing the normalized molecular interference function of water, the normalized molecular interference function of oxygenated water ($H_2O_2$), the normalized molecular interference function of acetone ($C_2H_6CO$), and the normalized molecular interference function of Plexiglas® (($C_5O_2H_8$)n), with, along the y-axis the number of photons detected and, along the x-axis, the momentum transfer x in $nm^{-1}$.

In the manner of the interferences determined by Bragg's law for a crystalline material, interference phenomena may also occur between the atoms and/or molecules of an amorphous material such as a liquid, this time involving a known distribution of distances (molecular interference function, denoted MIF). As a matter of fact, many amorphous materials have regular arrangements over nanometric distances (the expression short-range order used). This type of order is determined by strong chemical bonds for the covalent and ionic bonds. This short-range order causes intramolecular and intermolecular interferences. Appended FIG. 2 illustrates examples of molecular interference functions, i.e. the normalized MIF for water ($H_2O$), the normalized MIF for oxygenated water ($H_2O_2$), the normalized MIF for acetone ($C_2H_6CO$), and the normalized MIF of a material known under the tradename Plexiglas® (($C_5O_2H_8$)n).

The most common diffractometers are referred to as ADXRD (acronym for "Angular Dispersive X-ray Diffraction"). The energy is fixed by the use of monochrome radiation and the number of photons diffracted is measured according to the angle. Although these devices are very accurate, they require the use of a powerful monochrome source and cannot be used for imaging on account of their bulk.

Developed more recently, the EDXRD technique (EDXRD being the acronym for "Energy Dispersive X-Ray Diffraction") enables these difficulties to be alleviated. This time they consist in working at a fixed angle and using a set of collimators to illuminate the object with a polychromatic beam to measure the diffracted photons with an energy resolved spectrometric detector. The diffraction peaks then appear at certain energies in the measured spectrum.

The EDXRD technique, and more generally any technique of analysis by spectrometry, requires the employment of a spectrometric detector that is sufficiently energy resolving to enable the separation and the identification of the different characteristic peaks of the material constituting the object to analyze. The known detectors having the best energy resolution are of the Germanium type. However, this type of detector must be cooled to very low temperatures, by complex and/or costly methods (thermoelectric cooling or cooling by a tank of liquid nitrogen). Also, the analysis devices employing such a detector are very bulky.

The recent emergence of spectrometric detectors capable of being used at ambient temperature, such as detector types implementing CdTe, CdZnTe, or scintillator materials, provides an attractive alternative to the Germanium detectors. To be precise, these detectors are compact, not cooled and less costly. However, their performance in terms of energy resolution is still less than that obtained with the Germanium detectors, even though quite good.

To know whether a given crystalline or amorphous substance is contained in an object, it is thus known to:
  irradiate the object using an incident beam, emitted by a source of ionizing radiation, preferably collimated by a primary collimator,
  detect the diffracted radiation using a detection device comprising
    a detector, here termed spectrometric detector, configured to establish an energy spectrum (or spectrum of energy) of the radiation scattered at a given scattering angle, that is to say a detector comprising
    a detector material capable of interacting with radiation scattered by the object and which, on the near side to the object, presents what is referred to as a detection plane,
    a spectrometry measurement means, configured to measure an energy released by each interaction of a photon with the detector material and to establish at least one energy spectrum.
      a collimator, referred to as detection collimator, associated with the detector, the detector and the detection collimator being arranged so as to have a detection axis D forming a scattering angle $\theta$ with the central axis Z of the incident beam,
  analyzing the measured spectrum or spectra by comparison with the energy spectrum of the substance searched for.

In general terms, an energy spectrum illustrates the energy distribution of radiation in the form of a histogram representing the number of photon interactions in the object (along the y-axis) according to the released energy (along the x-axis). Often, the energy axis is discretized into channels of width $2\,\delta E$, a channel $C_i$, centered on the energy $E_i$ corresponding to the energies comprised between $E_i - \delta E$ and $E_i + \delta E$.

Patent application WO2013098520 describes a device for analyzing a material based on the processing and the analysis of a scattering spectrum.

The invention is an improvement of such a method of analyzing a scattered spectrum, making it possible to have more precise information as to the signature of the object examined.

For this, the invention provides a method for analyzing an object using a detection system comprising a spectrometric detector, the method comprising the following steps:
  irradiating the object with incident photon radiation, using a source of electromagnetic radiation;
  acquiring an energy spectrum, referred to as measured scattering spectrum, scattered by the object at a given angle $\theta$ comprised between 1° and 15°, using the spectrometric detector, placed for scattering, The method according to the invention is characterized in that it further comprises the following steps:
  acquiring a spectrum of energy transmitted by the object, referred to as measured transmission spectrum, using a spectrometric detector placed for transmission; the spectrometric detector placed for transmission may be that used to acquire the measured scattering spectrum, and which is moved between its two acquisition operations, either manually, or automatically using configured mechanical and information technology means; as a variant, a detection system is used comprising an additional spectrometric detector, which is then placed permanently for transmission and is dedicated to the acquisitions of measured transmission spectra;
  reconstructing a function, referred to as signature, representative of the object, based both on the measured scattering spectrum and the measured transmission spectrum;
  comparing the signature so reconstructed with signatures of calibration materials stored in a database, for the purposes of identifying a material constituting the object.

The invention is thus based on the combined use of at least one scattering spectrum and a transmission spectrum. This combination makes it possible to obtain a more precise signature (Bragg peaks or Molecular Interference Function) of a material constituting the object.

Advantageously and according to the invention, the step of reconstructing a signature of the object implements a method based on an inverse problem type approach.

The implementation of a method based on an inverse problem type approach makes it possible to recover the signature specific to the material independently of the instrumentation factors so as to improve the identification of the material.

Advantageously, the step of reconstructing a signature of the object comprises an operation of constructing an overall response matrix A of the detection system, each term $A(j,k)$ of the overall response matrix A corresponding to a probability of detecting, with the detector placed for scattering, a photon of energy $j$ when the object produces a momentum transfer equal to $k$.

Generally the overall response matrix A establishes a relationship between energy detected by the detector placed for scattering and a parameter that is characteristic of elastic scattering of the material constituting the object analyzed, in particular the momentum transfer.

The overall response matrix A is produced taking into account:
  the spectrum measured by the spectrometric detector placed for transmission, referred to as transmission spectrum, this spectrum representing the radiation emitted by the source into the object examined,
  an angular response function establishing a relationship, for a given scattering angle, between the energy of a scattered radiation and a parameter that is characteristic of the elastic scattering of the radiation the object, in particular a momentum transfer.

According to an embodiment, the response matrix A is produced by estimating the spectrum of the radiation from the source after attenuation by the object, such a spectrum being estimated from the transmission spectrum, for example using a calibration matrix of the detector placed for transmission;

According to an embodiment, the response matrix A is produced taking into account a calibration matrix of the detector placed for scattering.

In a preferred embodiment, the spectrometric detector placed for scattering is arranged so as to present a detection axis forming, with a central axis of the incident radiation, a scattering angle θ comprised between 1° and 10° or even between 1° and 5°.

In the most effective version of the invention providing the most precise signatures, the step of reconstructing a signature of the object comprises a step of estimating an incident spectrum attenuated by the object using the spectrum measured for transmission. Given the small scattering angle, the inventors have found that the attenuation by the object, as appearing through the transmission spectrum, could be advantageously taken into account in the processing of the scattering spectrum.

In a preferred embodiment, the method of analysis according to the invention comprises a first prior step of calibrating a response matrix of the spectrometric detector placed for scattering, a second prior step of calibrating a response matrix of the spectrometric detector placed for transmission, and a third prior step of calibrating an angular response matrix of the detection system, it being possible for these first, second and third prior calibrating steps to be carried out in one order or in another, before any irradiation of an object to analyze.

The prior steps of calibrating the response matrices of the spectrometric detector placed for scattering and of the spectrometric detector placed for transmission are not necessary but are advantageous, since they take into account the degradation of the spectra due to the response of the detector. However, these steps are optional, in particular for detectors that are sufficiently energy resolving and when the response of a detector is judged to be satisfactory.

In a preferred embodiment, the first and second prior steps of calibrating are carried out by simulation using a simulation software application of Monte-Carlo type.

The response of a detector, whether it be the detector used for transmission or the detector used for scattering, may be refined by exposing the detector to a source of radiation that is monochromatic or comprises a small number of emission rays, for example $^{241}$Am or $^{57}$Co.

According to an additional possible feature, the measured transmission spectrum and the measured scattering spectrum are acquired in a same operation of irradiating the object, provided a detection system comprising two sensors is available.

As a variant and preferably, the analyzing method comprises two parts executed in two stages: a first part during which the measured transmission spectrum is acquired and further to which the meeting of a suspicion criterion is verified, and a second part during which the measured diffraction spectrum is acquired and the signature is reconstructed. In this variant, it is possible to use a detection system with two detectors or a detection system with a single detector (which is moved from one position to the other).

More specifically, the first part of such a method in two stages comprises the following steps:
irradiating the object and acquiring a measured transmission spectrum,
determining a first characteristic of the object from the measured transmission spectrum; this first characteristic of the object may be a form, a dimension, an attenuation contrast, an effective atomic number $Z_{eff}$ of a material constituting the object;
Verifying the meeting of at least one suspicion criterion relating to the first characteristic of the object and expressing the fact that the object contains a potentially suspicious material for an application considered; thus for example, in the case of an application relating to the field of security such as the search for explosives in baggage, the suspicion criterion expresses the fact that the object contains a material of which the first characteristic is similar to that of an explosive material; in the case of a medical application such as the search for a tumor in a breast, the suspicion criterion expresses the fact that the object contains a material of which the first characteristic is close to that of a cancerous tissue. The suspicion criterion preferably defines a range of values of the first characteristic within which it is considered that the object is potentially suspicious, having regard to the application considered, and outside of which the object is considered as not being suspicious. The step of verifying the meeting of the suspicion criterion then comprises a comparison between the first characteristic determined for the object and the predetermined range of values having regard for the application considered.

The second part of the method in two stages is executed only when the suspicion criterion is met and comprises:
irradiating the object and acquiring a measured scattering spectrum,
reconstructing the signature of the object based on the measured scattering spectrum (acquired during this second part) and on the measured transmission spectrum (acquired during the first part), as explained earlier,
comparing the first characteristic of the object and its signature with characteristics and signatures of calibration materials stored in a database, for the purposes of identifying a material constituting the object.

Conversely, when the suspicion criterion is not met, the analysis method for the object is made to terminate at the end of the first part: the object in course of analysis is considered as inoffensive and is removed from the object receiving zone of the detection system. Where required, it is replaced by a new object to analyze.

The objective of the first part of such a method in two stages is not to identify the material constituting the object but to eliminate the objects that are clearly inoffensive (clear absence of explosive or clear absence of tumor or other unhealthy tissue, according to the application concerned) in order to save time, the second part of the method (longer since it requires the acquisition of a scattering spectrum) only being carried out on the potentially suspicious objects. The measured transmission spectrum is used twice in this version of the method according to the invention: a first time in the first part of the method for determining a characteristic of the object (form, dimension, effective atomic number, etc.) on which the suspicion criterion is based, and a second time in the second part of the method for reconstructing the signature.

SUMMARY

The invention covers a detection system provided to implement the method according to the invention, and in particular a detection system for the analysis of an object comprising:
a source of photon radiation,
a receiving zone for an object to analyze, a spectrometric detector placed for scattering downstream of this object receiving zone, for acquiring an energy spectrum, referred to as measured scattering spectrum, scattered by the object at a scattering angle θ comprised between 1° and 15°, The detection system according to the invention is characterized in that it comprises:
  an spectrum of energy transmitted by the object, referred to as measured transmission spectrum, which may be acquired either by an additional spectrometric detector placed for transmission downstream of the object receiving zone, or by the detector mentioned in the previous paragraph (serving for the acquisition of the measured scattering spectrum) and placed for transmission in advance.
  computer processing means comprising means for reconstructing a function, referred to as signature, representative of the object, from the measured scattering spectrum and from the measured transmission spectrum, and means for comparing the reconstructed signature with signatures of calibration materials stored in a database for the purposes of identifying a material constituting the object.

The detection system according to the invention further comprises, preferably, one or more of the following features:
  It comprises an additional spectrometric detector placed for transmission as previously referred to.
  The computer processing means are configured to implement a method based on an inverse problem type approach.
  The computer processing means are configured to estimate an overall response matrix of the detection system.
  The computer processing means are configured to estimate an overall response matrix (A) of the detection system from an estimated attenuated incident spectrum and from a calibrated angular response matrix of the detection system as well as, possibly, from a calibrated response matrix of the spectrometric detector placed for scattering and from a calibrated response matrix of the spectrometric detector placed for transmission.
  The computer processing means are configured to estimate an incident spectrum attenuated by the object using the spectrum measured for transmission.
  The radiation source is polychromatic.
  The radiation source is a source of X-rays.
  The spectrometric detector placed for scattering is configured so as to present a detection axis forming, with a central axis of the incident radiation, a scattering angle θ comprised between 1° and 10° and preferably between 1° and 5°.
  The detection system comprises a first collimator, referred to as source collimator, placed between the photon radiation source and the object receiving zone, so as to collimate the radiation emitted by the source along a central axis Z.
  The detection system comprises a second collimator, referred to as scattering collimator, between the object receiving zone and the spectrometric detector placed for scattering, the scattering collimator having a central collimation axis D forming a scattering angle θ with the incident central axis Z, which scattering angle θ is preferably comprised between 1° and 5°.
  The spectrometric detectors used are direct conversion sensors, i.e. the X photons incident on the sensor are absorbed by a semiconductor (CdTe for example) and create a cloud of electron charges (typically 10000 electrons for one X photon of 60 keV). These charges are then collected by electrodes and form a transient electrical signal called a pulse. If the collection is complete, the integral of the measured pulse for each detected particle is proportional to its energy deposited in the semiconductor. An electronic circuit makes it possible to measure this integral. After digitization, the different measurements of photons of the same energy are summed, which makes it possible to reconstruct the spectrum of the X-rays that interacted with the irradiated object.

The computer processing means comprise
  means for determining a first characteristic of the object based on the measured transmission spectrum,
  and means for verifying a suspicion criterion relating to the first characteristic determined previously for the object and expressing the fact that the object contains a potentially suspicious material for a considered application, for example by comparison of the first characteristic with a predefined range of values having regard to the application considered.

The invention covers a detection system and a method of analyzing an object which are characterized in combination by all or some of the features mentioned above and below.

BRIEF DESCRIPTION OF THE DRAWING

Other details and advantages of the present invention will appear from the reading of the following description, which refers to the diagrammatic appended drawings and which relates to preferred embodiments, provided by way of non-limiting examples. In the drawings.

DETAILED DESCRIPTION

Figure 3:
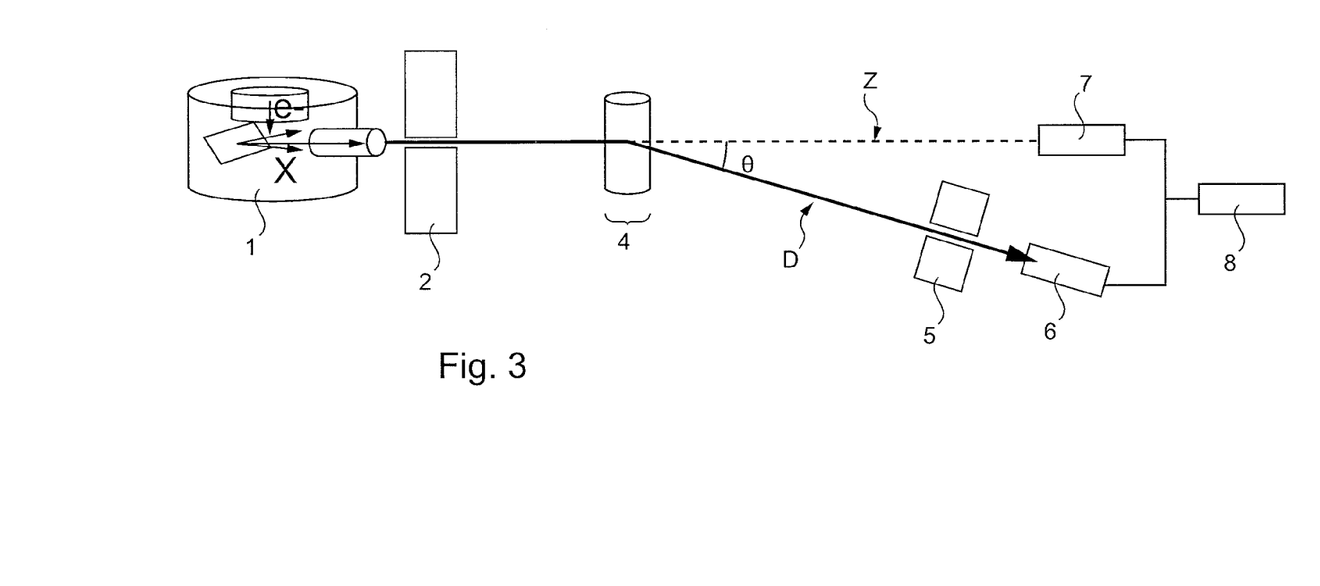
FIG. 3 is a diagrammatic view of a detection system according to the invention.

The detection system according to the invention illustrated in FIG. 3 comprises:
- a polychromatic source 1 of ionizing radiation, such as an X-ray tube,
- a source collimator 2, which makes it possible to channel the radiation from source 1 into an incident beam of incident central axis Z,
- a receiving zone 4 for an object to analyze;
- a scattering collimator 5 having a collimation axis D,
- a spectrometric detector 6 placed for scattering, which is associated with the scattering collimator 5 such that the detector 6 detects a radiation diffracted at a scattering angle θ (angle between the incident axis Z and the axis of collimation and detection D) for example equal to 2.5 (the representation in FIG. 3 not being to scale); the spectrometric detector 6 placed for scattering is configured to establish a measured spectrum (of energy) for scattering, that is to say an energy spectrum of the radiation diffracted by the object in the direction D; preferably, the spectrometric detector 6 placed for scattering is a semiconductor material based detector, such as a detector with CdTe or CdZnTe;
- a spectrometric detector 7 placed for transmission, configured to establish a measured transmission spectrum (of energy), that is to say an energy spectrum of the radiation transmitted by the object in the direction Z; preferably, the spectrometric detector 7 placed for transmission is a semiconductor material detector, such as a detector with CdTe or CdZnTe;
- computer processing means 8 for processing measured spectra supplied by the spectrometric detectors 6 and 7.

The terms "transmitted radiation" designate the radiation constituted by photons which have undergone no interaction in the examined object. By "transmission spectrum" is meant the radiation spectrum transmitted along the axis of the incident beam to the object, constituted by the photons which have undergone no interaction in the object. The expression "placed for transmission" designates a detector configured to detect the radiation transmitted by the material. Thus, a detector placed for transmission is situated on the axis of the radiation that is incident to the object, the object being placed between the detector and the radiation source.

By "spectrometric detector" is meant a detector configured to generate a spectrum of the detected radiation.

The method according to the invention is directed to providing a signature of a material constituting the object to analyze based on a measured scattering spectrum (provided by the spectrometric detector 6), the term "signature" designating a function representative of the material for scattering: Bragg peaks or Molecular Interference Function according to the nature—crystalline or amorphous—of the material.

This method preferably uses the following model, describing the relationship between the signature f of the material and the measured scattering spectrum g:

$$g = (R_{Ed} \times S_{inc} \times \text{Att}) \cdot R_\theta \cdot f = A \cdot f$$

With:

g: the vector of the measured (coherent) scattering spectrum, of size $(Nb_{Ejd} \times 1)$ $R_{Ed}$: the response matrix of the spectrometric detector placed for scattering, of size $(Nb_{Ejd} \times Nb_{Ei})$. In the case of a perfect detector, this matrix is a diagonal matrix. Each term $R_{Ed}(j,i)$ of the matrix represents the probability of detecting an energy value equal to j knowing that the radiation which is incident on the detector has an energy equal to i. In general, the response matrix of a spectrometric detector establishes a probabilistic relationship between an energy detected by the detector and the energy of the radiation that is incident on that detector. Each column i of $R_{Ed}(j,i)$, with j varying from 1 to $Nb_{Ejd}$, corresponds to the probability density of energy detected by the detector when the latter is subjected to incident radiation of energy i.

$S_{inc}$: vector of the incident spectrum of the X-ray tube of size $(1 \times Nb_{Ei})$;

Att: attenuation vector of size $(1 \times Nb_{Ei})$ which takes into account the effects of attenuation in the object. On account of the low value of the age θ, less than 15° and preferably less than 10°, the approximation will be made that the attenuation by the object along the path to the two detectors (for scattering and for transmission) is the same.

$R_\theta$: angular response matrix of the detection system, of size $(Nb_{Ei} \times Nb_x)$. Each term $R_\theta(j,k)$ of the matrix $R_\theta$ corresponds to a probability that the energy of a photon detected at the energy j corresponds to a momentum transfer equal to k. In other words, $R_\theta(j, k)$ corresponds to the probability that a momentum transfer k gives rise to the detection of a photon of energy j. Each column k $R_\theta(j,k)$, with j varying from 1 to $Nb_{Ejd}$, corresponds to the probability density of energy detected by the detector when there is a momentum transfer equal to k. More generally, the angular response matrix $R_\theta$ enables a probabilistic relationship to be established between the energy detected by the detector placed for scattering and an elastic scattering parameter of a material constituting the object, in particular a momentum transfer.

f: signature, of size $(1 \times Nb_x)$, specific to the material constituting the object, which makes it possible to describe either the theoretical Bragg peaks of the material in the case of a crystalline material, or the molecular interference function in the case of an amorphous material;

A: overall response matrix of the system for scattering, of size ($Nb_{Ejd} \times Nb_x$). Each term A(j,k) of A corresponds to a probability that the energy of a photon detected, by the detector for scattering, at the energy j corresponds to a momentum transfer equal to k. In other words, A(j,k) corresponds to the probability that a momentum transfer k gives rise to the detection of a photon at the energy j.

The symbol "×" corresponds to the term by term product ($S_{inc}$ and Att are multiplied term by term and a vector is then obtained which has the same size);

The symbol "." corresponds to the conventional matrix product;

$Nb_{Ejd}$, $Nb_{Ei}$ and $Nb_x$ respectively correspond to the number of channels of the measured scattering spectrum (that is to say to the number of channels of the energy spectrum detected by the detector placed for scattering), to the number of channels of the spectrum of the incident energy and to the number of channels of the vector describing the momentum transfer.

It is to be noted that the number of photons detected in each channel of the vector g follows a Poisson distribution having as parameter the average number of photons in that channel.

The originality of the method according to the invention is that it uses a measured transmission spectrum (provided by the spectrometric detector 7), of which the direct model is the following:

$$h = R_{Et} \cdot (S_{inc} \times Att)$$

With:

h: the vector of the measured transmission spectrum of size ($Nb_{Ejt} \times 1$)

$R_{Et}$: the response matrix of the spectrometric detector placed for transmission, of size ($Nb_{Ejt} \times Nb_{Ei}$). In the case of a perfect detector, this matrix is a diagonal matrix. Each term $R_{Et}$(j,i) of the matrix represents the probability of detecting an energy value equal to j when the photon which is incident on the detector has an energy i.

$S_{inc}$: the vector of the incident spectrum of the X-ray tube of size ($1 \times Nb_{Ei}$)

Att: the attenuation vector of size ($1 \times Nb_{Ei}$) which takes into account the effects of attenuation in the object, The vector ($S_{inc} \times Att$) represents the spectrum of the radiation source attenuated by the object. In the most effective version of the invention providing the most precise signatures, one of the key elements is to take into account this vector in the construction of the response matrix A of the system.

$Nb_{Ejt}$, $Nb_{Ei}$ respectively correspond to the number of channels of the measured transmission spectrum (that is to say to the number of channels of the energy spectrum detected by the detector placed for transmission) and to the number of channels of the incident energy spectrum.

The symbol × corresponds to the term by term product ($S_{inc}$ and Att are multiplied term by term and a vector is then obtained which has the same size).

The symbol . corresponds to the conventional matrix product.

The method according to the invention comprises an operation of constructing the overall response matrix A of the detection system, using the above model. For this, the terms $R_\Theta$, ($Sinc \times Att$), and, optionally, $R_{Ed}$ should be determined in advance.

Each of these steps is individually described later.

Once the overall response matrix A has been constructed using the aforementioned model, the method according to the invention reconstructs the signature f (molecular interface function for amorphous materials, distribution of the $d_{hkl}$ for the polycrystalline materials) based on the model $g = A \cdot f$ (where A and g are then known) by implementing a method based on an inverse problem type approach.

The Maximum Likelihood—Expectation Maximization algorithm (ML-EM) is available to estimate the spectrum to be calculated by iterative maximization of the function of log-likelihood. This type of calculation is very frequent when it is required to estimate a maximum likelihood, and relies on a more general algorithm, called Expectation—Maximization (EM). This method has the advantage of taking into account the Poisson-like nature of the measured data.

The coefficients of the overall response matrix A of the system are denoted $a_{i,j}$. It is wished to maximize the probability that the estimated f of dimension $Nb_x$ generates measurements g. It is furthermore known that the measured data follow a Poisson distribution, on account of their physical nature. The likelihood function of the estimated f can thus be written:

$$Pr(g/f) = \prod_{j=1}^{Nb_{Ejd}} \frac{e^{-\sum_{k=1}^{Nb_x} a_{j,k} f_k} \left( \sum_{k=1}^{Nb_x} a_{j,k} f_k \right)^{g_j}}{g_j!}$$

Its log-likelihood is then expressed $$\Phi(f) = \log Pr(g/f) = \sum_{j=1}^{Nb_{Ejd}} \left( -\sum_{k=1}^{Nb_x} a_{j,k} f_k + g_j \log \left( \sum_{k=1}^{Nb_x} a_{j,k} f_k \right) \right)$$

Next it is sought to maximize this function, by cancelling its derivative:

$$f_k \frac{\partial \phi(f)}{\partial f_k} = 0$$

The iterative solution of this problem is then written, with n designation the iteration:

$$f_k^{n+1} = f_k^n \frac{1}{\sum_{j=1}^{Nb_{Ejd}} a_{j,k}} \sum_{j=1}^{Nb_{Ejd}} \left( \frac{g_j a_{j,k}}{\sum_{k'=1}^{Nb_x} a_{j,k'} f_{k'}^n} \right)$$

By initializing the vector $f^{(0)}_k$ with positive values, it is ensured to have non-negative results.

Thus, based on an estimation of A and of the measurement of g, it is possible to reconstruct f by iterating the MLEM algorithm.

In other words, based on measurements made for transmission and for scattering on an unknown object, it is possible to reconstruct a function (i.e. a molecular interference function in the case of an amorphous material or Bragg peaks in the case of a crystalline material) relative to the structure of a material constituting the object. The values of this function are represented in the matrix A.

As this material is unknown, the objective is to identify it.

For this, a set of calibration materials is used (of explosive and non-explosive type in the case of an application for analyzing baggage for example; of healthy and malignant biological tissue type in the case of a medical analysis application) of which the signatures are tabulated and stored in a database, and the analysis method according to the invention next consists of comparing the values obtained for the object and of analyzing with those of the database, to identify the unknown object.

As a variant, some parameters making it possible to obtain structural parameters of the material are extracted from the signature reconstructed for the object; for example, in the case of a crystalline material, the extraction of the position of the peaks present in the signature obtained makes it possible to obtain the interplanar spacings of the crystal.

There are now described the various steps of the operation of constructing the overall response matrix A of the system.

Prior to any analysis of an object, that is to say "off-line", calibration operations are carried out to determine certain specifications of the detection system, which depend in particular on the detectors used and on the geometry of the system, and which, contrary to the attenuation vectors, do not depend on the object to analyze. These specifications are $R_{Et}$, $R_{Ed}$, $R_\theta$. They are next stored in the computer processing means 8.

The response matrix $R_{Et}$ of the spectrometric detector placed for transmission may be obtained from the Monte-Carlo Tasmania simulation software application, which makes it possible to simulate the whole detection chain of a semiconductor detector (photon interactions, transit of charge carriers, etc.). Preferably, this simulation is furthermore compared together with experimental data acquired for example with gamma sources. This makes it possible to adjust the energy resolution obtained on simulation.

Figure 4:
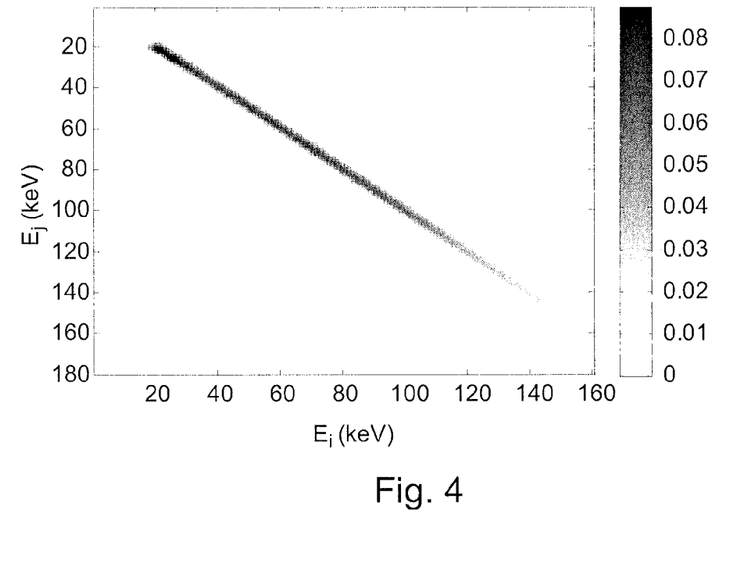
FIG. 4 is a graph representing the response matrix of the spectrometric detector placed for transmission of a detection system according to the invention such as that of FIG. 3.

FIG. 4 shows the response matrix $R_{Et}$ calibrated for the spectrometric detector 7 placed for transmission. This matrix defines the probability of detecting a photon at the energy Ej when the incident energy of the photon is Ei. This probability is indicated in FIG. 4 by gray tones (of which the scale has been transferred to the right of the graph), the x-axis of the graph representing the incident energy Ei expressed in keV, the y-axis corresponding to the detected energy Ej expressed in keV. In the case of a perfect detector, the matrix is diagonal (if it is square).

In similar manner, a prior operation of calibrating a response matrix $R_{Ed}$ of the spectrometric detector 6 placed for scattering is executed "off-line", by simulation using the Monte-Carlo simulation software application and/or by experiment.

Figure 5:
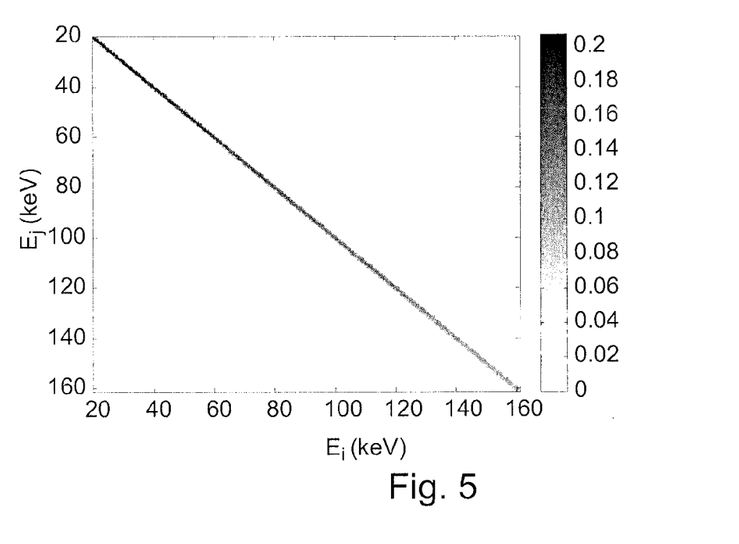
FIG. 5 is a graph representing the response matrix of the spectrometric detector placed for scattering of the detection system of FIG. 3.

The calibrated response matrix $R_{Ed}$ obtained is illustrated in FIG. 5. Here too, the x-axis represents the incident energy in keV, and the y-axis corresponds to the detected energy in keV, the probability of the pair (Ei, Ej) being expressed by gray tones.

A prior operation of calibrating an angular response matrix $R_\theta$ of the detection system is also executed "off-line". This angular response depends on the geometry of the acquisition system and more specifically on the opening of the source collimator 2 and to the opening of the scattering collimator 5, knowing that it is assumed that the object fills the intersection of two cones, i.e. an irradiation cone and an observation cone. The irradiation cone is defined by the solid angle under which the source irradiates the object, whereas the observation cone is defined by the solid angle under which the detector "sees" the object.

First of all an angular distribution 1D of the system is evaluated, either based on simulations, or based on calibrations. Using the relationship linking x (momentum transfer), E (energy that is incident on the detector placed for scattering) and θ (scattering angle), there is deduced the matrix of angular response function of Ei (incident Energy) and of x based on the angular distribution 1D function of θ.

Figure 6:
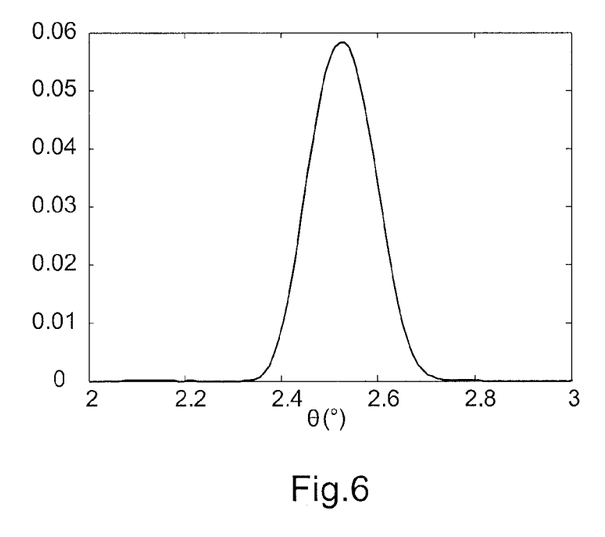
FIG. 6 is a graph representing the angular distribution of the spectrometric detector placed for scattering of the detection system of FIG. 3.
Figure 7:
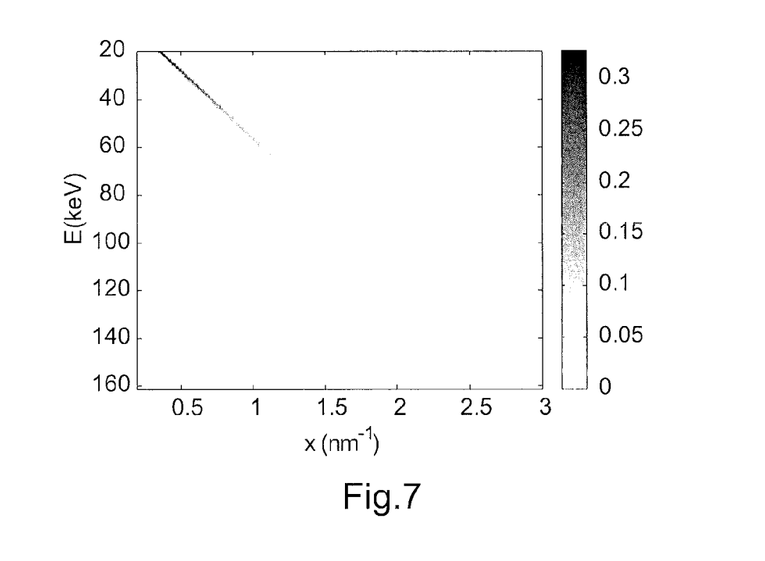
FIG. 7 is a graph representing the angular resolution matrix of the detection system of FIG. 3.

FIG. 6 shows an example of angular distribution 1D of the scattering system when the collimation axis D of the scattering collimator defines a scattering angle θ equal to 2.5°, the angular distribution expressing the relative quantity of photons that are incident on the detector placed for scattering (y-axis) according to the detection angle in degree (x-axis). This is an example since the use of collimators having different configurations (in particular width and length of the opening of the collimators) would lead to another graph being obtained. An angular response matrix $R_\theta$ of the detection system may be observed in FIG. 7, of which the x-axis represents the momentum transfer x in $nm^{-1}$, while the y-axis represents the energy E that is incident on the detector placed for scattering in keV, the gray tones expressing the relative quantity of incident photons. As referred to previously, this matrix defines a probabilistic relationship between the number of photons incident on the detector placed for scattering, at a given energy, and the momentum transfer.

The construction of the overall response A of the detection system using the model $A=(R_{Ed} \times S_{inc} \times Att) \cdot R_\theta$ still requires a step of estimating an incident spectrum attenuated by the object ($S_{inc} \times Att$).

Advantageously and according to the invention, this step of estimating the attenuated incident spectrum uses a transmission spectrum measured by a spectrometric detector placed for transmission. Such a transmission spectrum h may be written:

$$h = R_{Et} \cdot (S_{inc} \times Att)$$

In other words, it is considered, according to the invention, that the term ($S_{inc} \times Att$) in the expression of the matrix A is equal to the term ($S_{inc} \times Att$) in the expression of the transmission spectrum h. The inventors have shown that this approximation is entirely acceptable for scattering at small angles (less than 15°) and that it enables signatures f to be obtained of an excellent resolution and accuracy for scattering angles comprised between 1° and 5°.

To estimate ($S_{inc} \times Att$) based on the measured transmission spectrum h and on the calibrated response matrix $R_{Et}$ of the detector 7, the system according to the invention advantageously again uses a technique of MLEM type.

Figure 8:
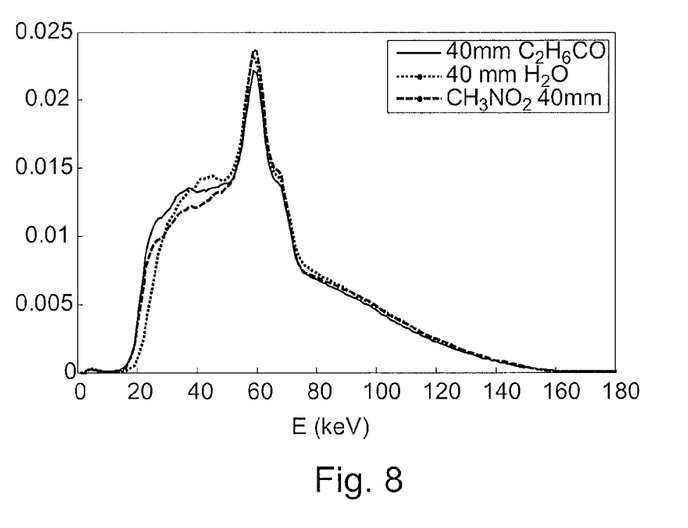
FIG. 8 is a graph representing transmission spectra for cylindrical samples of 40 mm diameter of acetone ($C_2H_6CO$), water ($H_2O$) and nitromethane ($CH_3NO_2$), as measured by the spectrometric detector placed for transmission of the detection system of FIG. 3.
Figure 9:
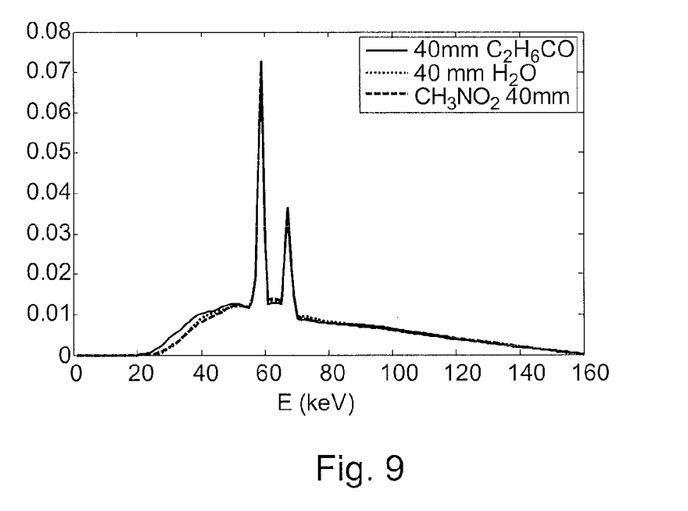
FIG. 9 is a graph representing estimated attenuated incident spectra for cylindrical samples of 40 mm diameter of acetone, water and nitromethane, as estimated according to the invention from measured transmission spectra of FIG. 8.

FIG. 9 shows different spectra ($S_{inc} \times Att$) obtained after MLEM inversion of the experimental data recorded on the spectrometric detector 7 placed for transmission, which data (measured spectra for transmission) are illustrated in FIG. 8, for a cylindrical sample of 40 mm diameter constituted respectively of water ($H_2O$), acetone ($C_2H_6CO$), and nitromethane ($CH_3NO_2$).

Figure 10:
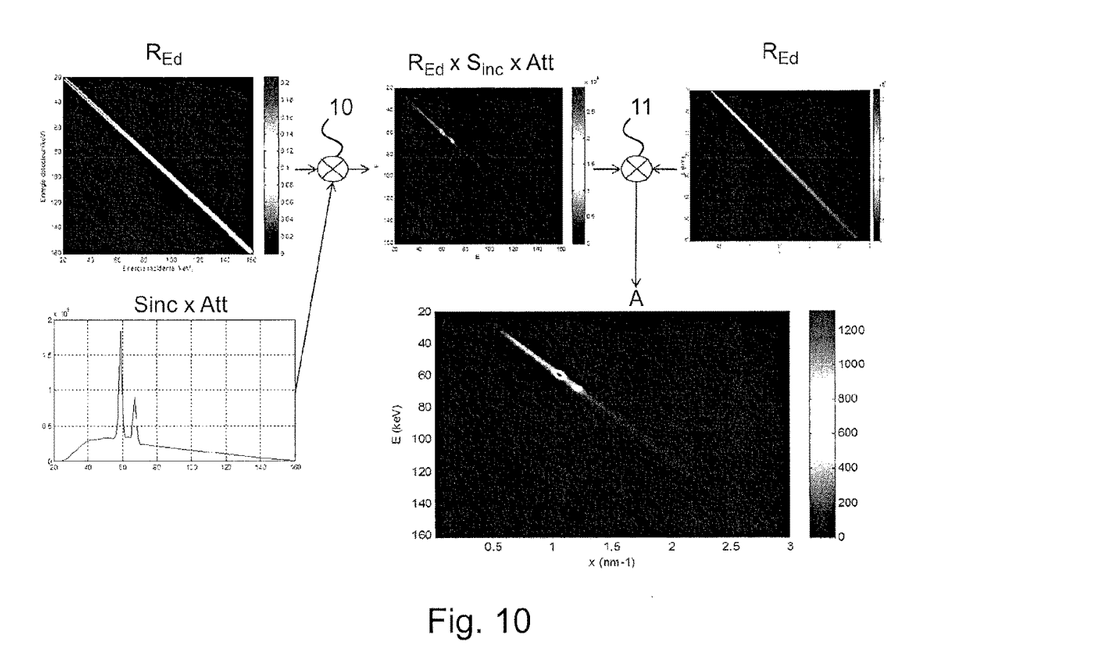
FIG. 10 is a diagram illustrating an operation of constructing an overall response of a detection system according to the invention such as that of FIG. 3.
Figure 11:
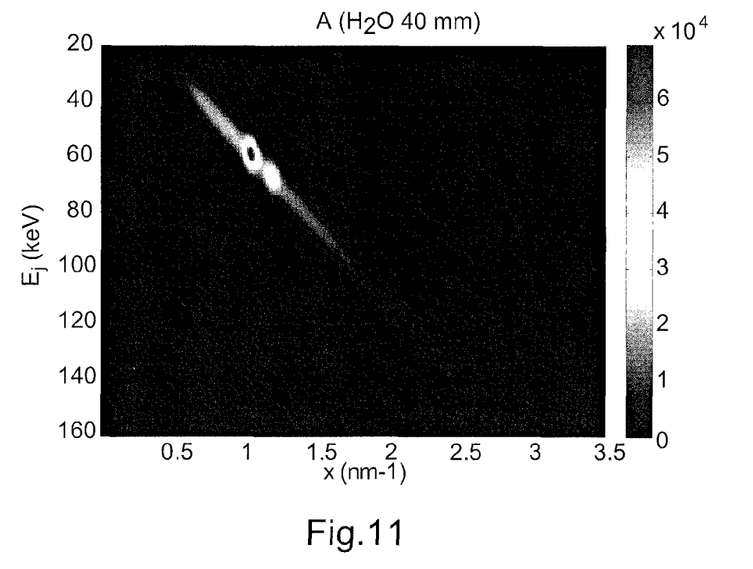
FIG. 11 is a graph representing the overall response matrix A of the detection system of FIG. 3 for a cylindrical sample of water of 40 mm diameter.
Figure 12:
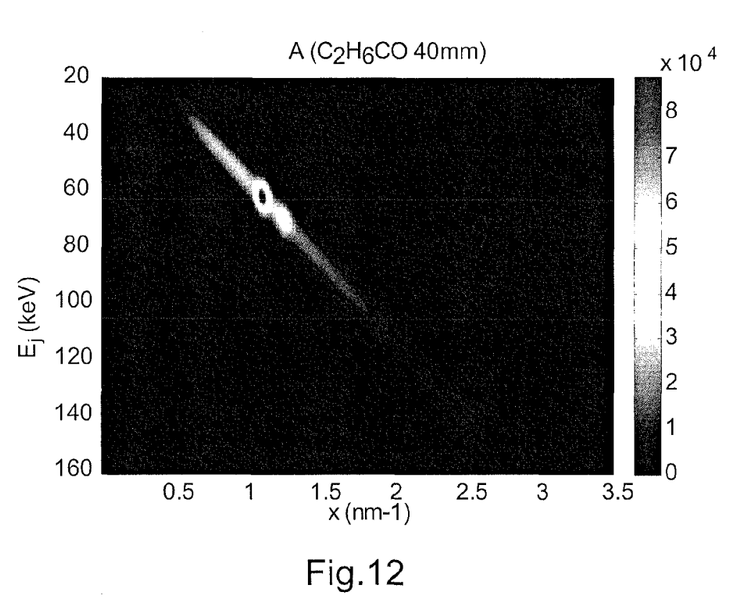
FIG. 12 is a graph representing the overall response matrix A of the detection system of FIG. 3 for a cylindrical sample of acetone of 40 mm diameter.

All the terms of the overall response matrix A of the system have been calibrated, the method according to the invention taken as example next consists of combining them according to the formula $A=(R_{Ed} \times S_{inc} \times Att) \cdot R_\theta$. This combination is summarized in FIG. 10 in which the numerical reference 10 designates a row by row multiplication and in which the numerical reference 11 designates a matrix multiplication.

The method according to the invention uses a detector placed for transmission which is a spectrometric detector. In the interest of economy and to limit the acquisition times, it could be attempted to use, instead of this spectrometric detector, a simple integration detector making it possible to record the number of photons transmitted through the object (independently of the energy released). The overall response matrix of the detection system could then be written $A=k \cdot R_{Ed} \cdot R_\theta$ in which k would be given by the signal for integration delivered by the detector placed for transmission.

The inventors have shown that this solution is to be ruled out.

Figure 14:
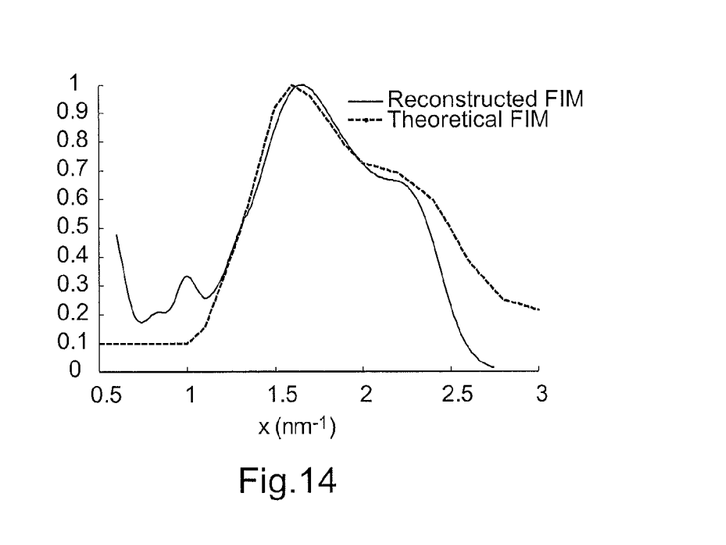
FIG. 14 is a graph representing the theoretical scattering signature (FIM) of a sample of water and the signature of that sample reconstructed from a measured scattering spectrum for the sample by using a method and a detection system according to the invention.

FIG. 14 reproduces the theoretical signature (molecular interference function) for a sample of water and the signature f obtained for this same sample of water according to the invention, that is to say by using a spectrometric detector placed for transmission and using, in this case, the model given by the formula $A=(R_{Ed} \times S_{inc} \times Att) \cdot R_\theta$ as well as a MLEM algorithm with 100 iterations for the inversion of $g=A \cdot f$. It may be noted that the two curves more or less coincide over a large part of the field of momentum transfer represented.

Figure 15:
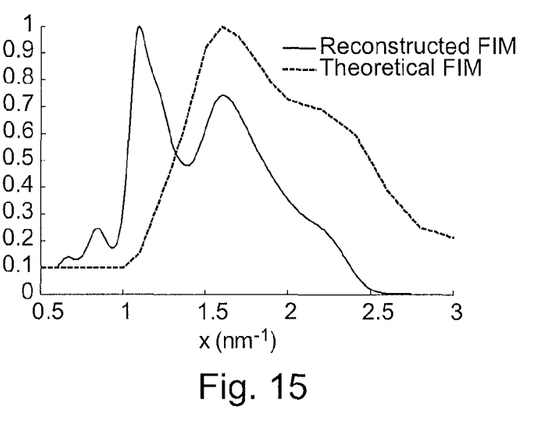
FIG. 15 is a graph representing the theoretical scattering signature (FIM) of a sample of water and the signature of that sample reconstructed from a measured scattering spectrum for the sample without taking into account the attenuation of the incident spectrum.

FIG. 15 reproduces the theoretical signature of the sample of water and the signature obtained for that same sample using an integration detector placed for transmission and using the model given by the formula $A=k \cdot R_{Ed} \cdot R_\theta$.

It may be noted that the two curves are very different over the whole of the field of momentum transfer represented and that the signature so reconstructed shows peaks which do not exist in the theoretical signature, such that it is not possible based on the signature so reconstructed to deduce that the sample is constituted by water.

By contrast, the invention is not limited to the model provided in the preferred example described above for the construction of the overall response matrix A of the detection system.

Thus for example, it may be envisioned to directly use the measured transmission spectrum without inversion of it to construct the overall response matrix A. In this case:

$$A=(R_{Ed} \times h) \cdot R_\theta = (R_{Ed} \times (R_{Et} \cdot (S_{inc} \times Att))) \cdot R_\theta$$

Figure 13:
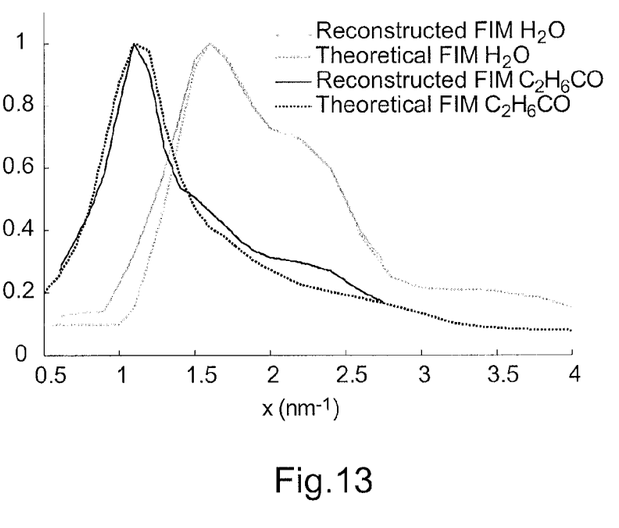
FIG. 13 is a graph representing the theoretical scattering signature (FIM) of a cylindrical sample of water of 40 mm diameter, and the signature of that sample as reconstructed by a method and by a detection system according to the invention, and also representing the theoretical scattering signature (FIM) of a cylindrical sample of acetone of 40 mm diameter, and the signature of that sample as reconstructed by a method and by a detection system according to the invention.

This variant is in accordance with the invention despite providing imperfect results. However, the inversion of the measured transmission spectrum in the preferred example described earlier, to remove the effect of the detector response, enables the results of the reconstruction of the signature to be greatly improved and to get as close as possible to the theoretical scattering signature of the object (cf. FIGS. 13 and 14).

The invention claimed is:

1. A method of analyzing an object using a detection system comprising a first spectrometric detector, the method comprising:
   irradiating the object with incident photon radiation;
   acquiring a measured scattering energy spectrum scattered by the object at a scattering angle ($\theta$) comprising between 1° and 15° using the first spectrometric detector, placed for scattering;
   acquiring a measured transmission spectrum of energy transmitted by the object, using a second spectrometric detector placed for transmission;
   reconstructing a signature function (f) representative of the object, based on both the measured scattering energy spectrum and the measured transmission spectrum and estimating an incident spectrum attenuated by the object using the measured transmission spectrum; and
   comparing the signature function with signatures of calibration materials stored in a database for the purposes of identifying a material constituting the object.

2. The analyzing method according to claim 1, wherein reconstructing the signature function of the object comprises an operation of constructing an overall response matrix (A) of the detection system that establishes a relationship between an energy detected by the first spectrometric detector placed for scattering and a momentum transfer.

3. The analyzing method according to claim 2, wherein the operation of constructing the overall response matrix (A) of the detection system is made on the basis of an estimated attenuated incident spectrum (Sinc×Att) and of a calibrated angular response matrix ($R_\theta$) of the detection system.

4. The analyzing method according to claim 3, wherein the operation of constructing the overall response matrix (A) of the detection system is furthermore made on the basis of a calibrated response matrix ($R_{Ed}$) of the first spectrometric detector placed for scattering, and of a calibrated response matrix ($R_{Et}$) of the second spectrometric detector placed for transmission.

5. The analyzing method according to claim 1, wherein the first spectrometric detector placed for scattering is configured so as to present a detection axis (D) forming, with a central axis (Z) of the incident radiation, a scattering angle ($\theta$) comprised between 1° and 5°.

6. The analyzing method according to claim 1 further comprising:
   first calibrating a response matrix ($R_{Ed}$) of the first spectrometric detector placed for scattering (6);
   second calibrating a response matrix ($R_{Et}$) of the second spectrometric detector placed for transmission; and
   third calibrating an angular response matrix ($R_\theta$) of the detection system, wherein the first, second and third calibrating steps are carried out irradiating the object.

7. The analyzing method according to claim 6, wherein the first and second calibrating steps are carried out by simulation using a simulation software application of a Monte-Carlo type.

8. The analyzing method according to claim 7, wherein the response matrix of the first spectrometric detector placed for scattering obtained by simulation is refined using at least one measurement of a spectrum scattered by a calibration material irradiated by a source of gamma rays, in the same way as the response matrix of the first spectrometric detector placed for transmission obtained by simulation is refined using at least one measurement of a spectrum transmitted by a calibration material irradiated by a source of gamma rays.

9. A detection system for analyzing an object comprising:
   a source of photon radiation;
   a zone for the reception of an object to analyze;
   a detector apparatus downstream of the zone that acquires an measured scattering energy spectrum scattered by the object at a scattering angle ($\theta$) comprising between 1° and 15°, and that acquires a measured transmission spectrum of energy transmitted by the object;
   a computer processing means for reconstructing a signature function (f), representative of the object, from the measured scattering spectrum and from the measured transmission spectrum that includes estimating an incident spectrum attenuated by the object using the measured transmission spectrum, and for comparing the reconstructed signature function (f) with signatures of calibration materials stored in a database for the purposes of identifying a material constituting the object.

10. The detection system according to claim 9, wherein the detector apparatus comprises a first spectrometric detector for acquiring the measured scattering energy spectrum, and a second spectrometric detector for acquiring the measured transmission spectrum.

11. The detection system according to claim 9, wherein the computer processing means is further configured to implement a method based on an inverse problem type approach and to construct an overall response matrix (A) of the detection system, which the overall response matrix (A) establishes a relationship between an energy detected by the spectrometric detector placed for scattering and a momentum transfer.

12. The detection system according to claim 11, wherein the overall response matrix (A) of the detection system is constructed from:
- an attenuated incident spectrum (Sinc×Att) estimated using the measured transmission spectrum, and
- a calibrated angular response matrix ($R_\theta$) of the detection system.

13. The detection system according to claim 12, wherein the overall response matrix (A) of the detection system is further constructed from:
- a calibrated response matrix ($R_{Ed}$) of the spectrometric detector (6) placed for scattering, and
- a calibrated response matrix ($R_{Et}$) of the spectrometric detector (7) placed for transmission.

14. The detection system according to claim 9, wherein the first spectrometric detector placed for scattering is configured so as to present a detection axis (D) forming, with a central axis (Z) of the incident radiation, a scattering angle ($\theta$) comprising between 1° and 5°.

\* \* \* \* \*